United States Patent
Matur et al.

(10) Patent No.: US 11,413,235 B2
(45) Date of Patent: Aug. 16, 2022

(54) ORAL CARE COMPOSITIONS

(71) Applicant: GABA International Holding GmbH, Therwil (CH)

(72) Inventors: Turan Matur, Binningen (CH); Sylvia Hess, Holstein (CH); Andre Brunella, Dornach (CH); Thomas Schollbach, Basel (CH)

(73) Assignee: Colgate-Palmolive Company, New York, NY (US)

( * ) Notice: Subject to any disclaimer, the term of this patent is extended or adjusted under 35 U.S.C. 154(b) by 43 days.

(21) Appl. No.: 16/956,678

(22) PCT Filed: Dec. 22, 2017

(86) PCT No.: PCT/EP2017/084299
§ 371 (c)(1),
(2) Date: Jun. 22, 2020

(87) PCT Pub. No.: WO2019/120559
PCT Pub. Date: Jun. 27, 2019

(65) Prior Publication Data
US 2020/0330362 A1 Oct. 22, 2020

(51) Int. Cl.
| | | |
|---|---|---|
| *A61K 8/86* | (2006.01) | |
| *A61K 8/362* | (2006.01) | |
| *A61K 8/365* | (2006.01) | |
| *A61K 8/368* | (2006.01) | |
| *A61K 8/41* | (2006.01) | |
| *A61Q 11/00* | (2006.01) | |

(52) U.S. Cl.
CPC .............. *A61K 8/86* (2013.01); *A61K 8/362* (2013.01); *A61K 8/365* (2013.01); *A61K 8/368* (2013.01); *A61K 8/41* (2013.01); *A61Q 11/00* (2013.01)

(58) Field of Classification Search
CPC .......... A61K 8/86; A61K 8/362; A61K 8/365; A61K 8/368; A61K 8/41; A61Q 11/00
See application file for complete search history.

(56) References Cited

U.S. PATENT DOCUMENTS

| | | | |
|---|---|---|---|
| 5,518,993 A | 5/1996 | Lee et al. | |
| 2014/0377194 A1* | 12/2014 | Strand | A61Q 11/00 424/57 |

FOREIGN PATENT DOCUMENTS

| | | |
|---|---|---|
| CH | 603158 | 8/1978 |
| EP | 1757674 | 2/2007 |
| WO | 2016/100628 | 6/2016 |

OTHER PUBLICATIONS

International Search Report and Written Opinion of the International Searching Authority in International Application No. PCT/EP2017/084299, dated Feb. 26, 2018.

* cited by examiner

*Primary Examiner* — Snigdha Maewall

(57) ABSTRACT

Described herein are liquid compositions, comprising an ethoxylated amine of a fatty acid, an organic solvent, and an acid.

16 Claims, No Drawings

ORAL CARE COMPOSITIONS

BACKGROUND

Ethoxylated amines of fatty acids are used in a variety of oral care, home care, and personal care applications. For example, ethoxylated amines are used as surfactants, emollients, fluoride carriers, and preservatives. One example, Olaflur, is a fluoride-containing ethoxylated amine of mainly stearic acid used in toothpastes since the 1960s.

Ethoxylated amines are usually formed as sticky solids and are therefore not easy to handle in many manufacturing processes. In addition, ethoxylated amines may also include a variety of byproducts and impurities which are difficult to remove under current purification methods, such as distillation or crystallization.

In order to facilitate production of products containing ethoxylated amines, it is preferred that the ethoxylated amines are provided as liquid compositions, and especially, as liquid compositions that are stable at room temperature and that can be used in aqueous preparations. However, ethoxylated amines are often poorly soluble in water, and may be unable to form stable solutions in other solvents. While solutions of ethoxylated amines in ethanol are known, these are not preferred for use in the production of alcohol-free formulations. Similarly, while ethoxylated amines may also be dissolved in other organic solvents, these solutions often display precipitation and/or separation upon storage and slow dissolutions or non-ideal dispersion when used for aqueous preparations.

Accordingly, there is a need for liquid compositions of ethoxylated amines that are alcohol-free, stable at room temperature and during storage, and which comprise high amounts of ethoxylated amine and low amounts of byproducts that can be used in aqueous preparations.

BRIEF SUMMARY

This summary is intended merely to introduce a simplified summary of some aspects of one or more embodiments of the present disclosure. Further areas of applicability of the present invention will become apparent from the detailed description provided hereinafter. This summary is not an extensive overview, nor is it intended to identify key or critical elements of the present teachings, nor to delineate the scope of the disclosure. Rather, its purpose is merely to present one or more concepts in simplified form as a prelude to the detailed description below.

The foregoing and/or other aspects and utilities embodied in the present disclosure may be achieved by providing liquid composition, including from 10 weight % to 55 weight % of ethoxylated amine of a fatty acid, based on a total weight of the liquid composition; from 35 weight % to 75 weight % of organic solvent, based on the total weight of the liquid composition; and from 0.20 weight % to 25 weight % of acid, based on the total weight of the liquid composition.

In another embodiment, the ethoxylated amine of a fatty acid includes a C12-C22 saturated alkyl amine.

In another embodiment, the ethoxylated amine of a fatty acid includes an unsaturated alkyl amine.

In another embodiment, the ethoxylated amine of a fatty acid includes PEG-2 Stearamine.

In another embodiment, the ethoxylated amine of a fatty acid includes PEG-3 Tallow Aminopropylamine.

In another embodiment, the ethoxylated amine of a fatty acid includes 70% or more PEG-2 Stearamine.

In another embodiment, the PEG-2 Stearamine is produced from plant-derived stearic acid.

In another embodiment, the PEG-2 Stearamine is produced from the primary amine of stearic acid ethoxylated with ethylene oxide at an ethylene oxide:primary amine ratio of 2.0 to 2.20:1

In another embodiment, the organic solvent includes propylene glycol.

In another embodiment, the liquid composition includes from 30 weight % to 55 weight % ethoxylated amine, optionally, the liquid composition includes from 35 weight % to 45 weight % organic solvent, and, further optionally, the liquid composition includes from 5 weight % to 15 weight % acid.

In another embodiment, the acid is one or more acids selected from the group consisting of malic acid, benzoic acid, mandelic acid, lactic acid, acetic acid, succinic acid, tartaric acid, and citric acid.

In another embodiment, the acid is one or more of malic acid, mandelic acid, lactic acid, acetic acid, succinic acid, tartaric acid, and citric acid.

In another embodiment, the acid is one or more of malic acid, lactic acid, and tartaric acid.

In another embodiment, the acid is malic acid or tartaric acid.

In another embodiment, the acid is a combination of malic acid and benzoic acid and/or mandelic acid.

In another embodiment, the liquid composition is alcohol-free.

In another embodiment, the liquid composition consists essentially of PEG-2 Stearamine; propylene glycol; and the acid consists essentially of malic acid, tartaric acid, or mixtures thereof.

In another embodiment, the liquid composition is stable and free of precipitates after two weeks of storage at room temperature.

In another embodiment, the liquid composition is stable and free of precipitates after three months of storage at room temperature.

DETAILED DESCRIPTION

Reference will now be made in detail to the various embodiments in the present disclosure. The embodiments are described below to provide a more complete understanding of the components, processes, compositions, and apparatuses disclosed herein. Any examples given are intended to be illustrative, and not restrictive. However, it will be apparent to one of ordinary skill in the art that the invention may be practiced without these specific details. In other instances, well-known methods, procedures, and components have not been described in detail so as not to unnecessarily obscure aspects of the embodiments.

Throughout the specification and claims, the following terms take the meanings explicitly associated herein, unless the context clearly dictates otherwise. The phrases "in some embodiments" and "in an embodiment" as used herein do not necessarily refer to the same embodiment(s), though they may. Furthermore, the phrases "in another embodiment" and "in some other embodiments" as used herein do not necessarily refer to a different embodiment, although they may. As described below, various embodiments may be readily combined, without departing from the scope or spirit of the present disclosure.

As used herein, the term "or" is an inclusive operator, and is equivalent to the term "and/or," unless the context clearly dictates otherwise. The term "based on" is not exclusive and allows for being based on additional factors not described, unless the context clearly dictates otherwise. In the specification, the recitation of "at least one of A, B, and C," includes embodiments containing A, B, or C, multiple examples of A, B, or C, or combinations of A/B, A/C, B/C, A/B/B/B/B/C, A/B/C, etc. In addition, throughout the specification, the meaning of "a," "an," and "the" include plural references. The meaning of "in" includes "in" and "on."

It will also be understood that, although the terms first, second, etc. may be used herein to describe various elements, these elements should not be limited by these terms. These terms are only used to distinguish one element from another. For example, a first object, component, or step could be termed a second object, component, or step, and, similarly, a second object, component, or step could be termed a first object, component, or step, without departing from the scope of the invention. The first object, component, or step, and the second object, component, or step, are both, objects, component, or steps, respectively, but they are not to be considered the same object, component, or step. It will be further understood that the terms "includes," "including," "comprises" and/or "comprising," when used in this specification, specify the presence of stated features, steps, operations, elements, and/or components, but do not preclude the presence or addition of one or more other features, steps, operations, elements, components, and/or groups thereof. Further, as used herein, the term "if" may be construed to mean "when" or "upon" or "in response to determining" or "in response to detecting," depending on the context.

All physical properties that are defined hereinafter are measured at 20° to 25° Celsius unless otherwise specified.

When referring to any numerical range of values herein, such ranges are understood to include each and every number and/or fraction between the stated range minimum and maximum, as well as the endpoints. For example, a range of 0.5-6% would expressly include all intermediate values of, for example, 0.6%, 0.7%, and 0.9%, all the way up to and including 5.95%, 5.97%, and 5.99%, among many others. The same applies to each other numerical property and/or elemental range set forth herein, unless the context clearly dictates otherwise.

Additionally, all numerical values are "about" or "approximately" the indicated value, and take into account experimental error and variations that would be expected by a person having ordinary skill in the art. It should be appreciated that all numerical values and ranges disclosed herein are approximate values and ranges, whether or not "about" is used in conjunction therewith.

Unless otherwise specified, all percentages and amounts expressed herein and elsewhere in the specification should be understood to refer to percentages by weight. The amounts given are based on the active weight of the material.

With regard to procedures, methods, techniques, and workflows that are in accordance with some embodiments, some operations in the procedures, methods, techniques, and workflows disclosed herein may be combined and/or the order of some operations may be changed.

According to some embodiments, the present disclosure provides a stable liquid composition including an ethoxylated amine, an organic solvent, and an acid.

The liquid composition includes the ethoxylated amine of a fatty acid. In certain embodiments, the ethoxylated amine of a fatty acid may be a C12-C22 saturated alkyl amine. In other embodiments, the ethoxylated amine may also be an unsaturated alkyl amine, either alone or as a mixture with saturated alkyl amines. In certain embodiments, the ethoxylated amine may be a non-liquid material that is not readily soluble in water. The ethoxylated amine may be derived from stearic acid. For example, the ethoxylated amine may include a 2,2'-(octadecylimino)bisethanol, such as a PEG-2 Stearamine (CAS: 10213-78-2). In other embodiments, the ethoxylated amine may include 2,2'-(hexadecylimino)bisethanol derived from palmitic acid and/or PEG-3 Tallow Aminopropylamine (N,N,N'-tris (2-hydroxyethyl)-N'-alkyl/alkenyl(C14-C18)-1,3-diaminopropane), which contains a mixture of C14-C18 saturated and unsaturated fatty acids (CAS: 90367-27-4).

In certain embodiments, the ethoxylated amine has a high ratio of the target ethoxylated amine content. For example, when the target ethoxylated amine is PEG-2 Stearamine, the ethoxylated amine includes 70% or more PEG-2 Stearamine. That is, the PEG-2 Stearamine component of the liquid composition has a 70% or more purity level. In other embodiments, the ethoxylated amine has an 80% or more ethoxylated amine content or 90% or more ethoxylated amine content.

In certain embodiments, the ethoxylated amine is produced from plant-derived fatty acids. For example, the ethoxylated amine may be a PEG-2 Stearamine produced from plant-derived stearic acid.

In certain embodiments, the ethoxylated amine is produced from a fatty acid converted to an amine and then reduced catalytically with ethylene oxide to produce the primary amine. The primary amine is then ethoxylated to create the ethoxylated amine. The ethoxylated amine may include a variety of byproducts created during the ethoxylation step, such as under-ethoxylated and over-ethoxylated primary amines. For example, PEG-1 Stearamine and PEG-3 Stearamine may be under and over ethoxylation byproducts of PEG-2 Stearamine. Similarly, PEG-2 Palmitylamine, PEG-2 Heptadecylamine, and PEG-2 Nonadecylamine may also be byproducts of PEG-2 Stearamine production.

In certain embodiments, the ethoxylation step is optimized to reduce the amount of byproducts created. For example, a ratio of ethylene oxide to the primary amine may be optimized to reduce the formation of secondary amines, such as nitrosamines, (under-ethoxylation) and/or to reduce the formation of over-ethoxylated amines which may affect the taste and color of the ethoxylated amine and the liquid composition.

In one embodiment, the ratio of ethylene oxide to the primary amine is from 2.0 to 2.20:1. In other embodiments, the ratio of ethylene oxide to the primary amine is 2.10:1.

In certain embodiments, the ethoxylated amine includes 0.5% or less secondary amines. In other embodiments, the ethoxylated amine includes 0.4%, 0.3%, 0.2%, or 0.1% or less secondary amines.

The liquid composition may include 20% or more ethoxylated amine, based on a total weight of the liquid composition. In certain embodiments, the liquid composition may include 30 weight % or more ethoxylated amine, 40% weight % or more ethoxylated amine, or 50 weight % or more ethoxylated amine.

In other embodiments, the liquid composition may include up to 55% ethoxylated amine.

In certain embodiments, the liquid composition may include from 10 weight % to 55 weight % ethoxylated amine, from 20 weight % to 55 weight % ethoxylated amine, from 30 weight % to 55 weight % ethoxylated amine, or from 30 weight % to 55 weight % ethoxylated amine.

For example, the liquid composition may include up to 50% PEG-2 Stearamine, or may include from 10% to 50% or from 25% to 50% PEG-2 Stearamine. In other embodiments, the liquid composition may include from 10% to 50% PEG-2 Stearamine or from 25% to 50% PEG-2 Stearamine.

The liquid composition also includes an organic solvent. For example, the liquid composition may include a diol as an organic solvent. In certain embodiments, the organic solvent may include propylene glycol.

The liquid composition may include up to 90% organic solvent, based on a total weight of the liquid composition. In other embodiments, the liquid composition may include up to 85%, 80%, 75%, 70%, 65%, 60%, 55%, and 50% organic solvent, based on the total weight of the liquid composition. For example, the liquid composition may include up to 90%, 85%, 80%, 75%, 70%, 65%, 60%, 55%, and 50% propylene glycol. In certain embodiments, the liquid composition may include from 35% to 75% organic solvent, based on the total weight of the liquid composition. In other embodiments, the liquid composition may include from 35% to 45% organic solvent.

In some embodiments, the liquid composition does not contain monohydric alcohols. For example, in some embodiments the liquid composition excludes ethanol and is considered alcohol-free.

As used herein, the term "alcohol-free" means containing less than 5%, such as less than 4%, 3%, 2%, 1%, or 0.5%, of C1-C3 monohydric alcohols, such as methanol, ethanol, and propanol, based on the total weight of the liquid composition.

While ethoxylated amines can be dissolved in organic solvents, these solutions are not stable. For example, while PEG-2 Stearamine is soluble in propylene glycol, the solution is not stable and will separate upon aging at room temperature. Similarly, solutions of ethoxylated amines in other organic solvents, such as 1,3-propanediol, methylpropandiol, 1,3-butylene glycol, and isopentyldiol, create creamy or viscous and slightly turbid solutions that also separate or even resolidify upon storage and aging. However, the inventors have surprisingly discovered that specific acids can be used to stabilize ethoxylated amines dissolved in organic solvents. For example, the addition of specific acids to the liquid composition resulted in clear to turbid viscous solutions of ethoxylated amines in an organic solvent that do not separate upon aging and could therefore be used in manufacturing process. In certain embodiments, the addition of the acid improves the dissolution of the ethoxylated amine liquid composition in aqueous systems.

Accordingly, under the embodiments of the present disclosure, the liquid composition includes one or more acids. In certain embodiments, the liquid composition includes one or more acids selected from malic acid, benzoic acid, mandelic acid, lactic acid, acetic acid, succinic acid, tartaric acid, and citric acid.

In certain embodiments, the liquid composition includes only one acid selected from malic acid, mandelic acid, lactic acid, acetic acid, succinic acid, tartaric acid, and citric acid.

In other embodiments, the liquid composition includes one or more acids selected from malic acid, lactic acid, and tartaric acid. In certain embodiments, the liquid composition includes only one acid selected from malic acid, lactic acid, and tartaric acid.

In other embodiments, the liquid composition includes mixtures of malic acid with benzoic acid and/or mandelic acid. In certain embodiments, the liquid composition includes malic acid, tartaric acid, and combinations thereof.

The liquid composition may include 5% or more acid, based on a total weight of the liquid composition. For example, the composition may include a mixture of 3% malic acid and 20% mandelic acid. In other examples, the liquid composition may include 10 weight % or more acid, 15 weight % or more acid, or 20 weight % or more acid.

In certain embodiments, the liquid composition may include up to 25% acid, based on a total weight of the liquid composition.

In other embodiments, the liquid composition may include up to 15 weight %, up to 12 weight %, up to 10 weight %, up to 7.5 weight %, or up to 5 weight %, based on the total weight of the liquid composition. For example, the liquid composition may include up to 14 weight % malic acid and/or tartaric acid.

In certain embodiments, the liquid composition may include from 0.20% to 25% acid, based on the total weight of the liquid composition. In other embodiments, the liquid composition may include from 0.33 weight % to 25 weight % acid, from 0.5 weight % to 25 weight %, from 1 weight % to 25 weight %, from 4 weight % to 20%, from 5 weight % to 15 weight %, or from 8 weight % to 14 weight % acid, based on the total weight of the liquid composition.

In certain embodiments, the amount of acid in the liquid composition is based on a ratio with the organic solvent. For example, in one embodiment, the liquid composition includes an organic solvent to acid ratio of 1.5-5.0:1. In other embodiments, the liquid composition includes an organic solvent to acid ratio of 2.5-5.0:1, 3.5-5.0:1, or 4.5-5.0:1. In other embodiments, a ratio between the ethoxylated amine and the acid may be calculated stoichiometrically based on expected level of protonation of the ethoxylated base. For example, in certain embodiments, the amount of acid in the liquid composition is selected such that the amine groups in the ethoxylated amine should preferably be (almost) fully protonated by the acid. In one embodiment, the amount of acid is selected to ensure a protonation of 90% or greater in the ethoxylated amine.

In certain embodiments, the liquid composition does not separate and is stable as a flowable liquid and free of precipitates after 1 week of storage at room temperature. In other embodiments, the liquid composition does not separate and is stable as a flowable liquid and free of precipitates after 2 weeks, 4 weeks, 2 months, or 3 months of storage at room temperature. In certain embodiments, the liquid composition does not separate and remains stable as a flowable liquid after 12 months of storage at room temperature. In certain embodiments, the liquid composition does not separate, and is stable flowable liquid free of precipitates after at least 2 weeks, 4 weeks, 2 months, 3 months, 6 months, or 12 months of storage at room temperature. In certain embodiments, the liquid composition remains clear after at least 2 weeks, 4 weeks, 2 months, 3 months, 6 months, or 12 months of storage at room temperature.

EXAMPLE

Table 1 illustrates liquid compositions according to the present disclosure.

The liquid compositions 1-6 of Table 1 were prepared as follows: a PEG-2 Stearamine composition having 90% or more PEG-2 Stearamine was added to the propylene glycol. The mixture was heated to 50° C. while on a magnetic stirrer. Once the PEG-2 Stearamine and propylene glycol were a homogenous mixture, malic acid was added as a stabilizer. The mixture was stirred until the malic acid was completely dissolved. Then the mixture was cooled to room temperature. Comparative composition A was prepared in a similar manner, except malic acid was not added as a stabilizer.

TABLE 1

| | PEG-2 Stearamine | PEG-3 Tallow Aminopropylamine | Propylene Glycol | Malic Acid | Tartaric Acid |
|---|---|---|---|---|---|
| Composition 1 | 23% | — | 72% | 5% | — |
| Composition 2 | 23% | — | 73% | 4% | — |
| Composition 3 | — | 48% | 38.25% | 13.75% | — |
| Composition 4 | 48% | — | 38.25% | 13.75% | — |
| Composition 5 | — | 20% | 71.35% | 8.65% | — |
| Composition 6 | — | 20% | 72.90% | — | 7.10% |
| Comparative Composition A | 23% | — | 77% | — | — |

The compositions of Table 1 were then stored at room temperature for up to 12 months. When checked after 3, 6, and 12 months, the liquid compositions 1-6 were free from precipitates. In addition, the liquid compositions 1-6 had excellent flow characteristics and good dissolution when used in aqueous preparations. In contrast, comparative composition A was not stable, formed precipitates, and separated.

The present disclosure has been described with reference to exemplary embodiments. Although a few embodiments have been shown and described, it will be appreciated by those skilled in the art that changes may be made in these embodiments without departing from the principles and spirit of preceding detailed description. It is intended that the present disclosure be construed as including all such modifications and alterations insofar as they come within the scope of the appended claims or the equivalents thereof.

The invention claimed is:

1. A liquid composition, comprising:
   from 10 weight % to 55 weight % of either 2'-(octadecylimino)bisethanol or N,N,N'-tris(2-hydroxyethyl)-N'-alkyl/alkenyl(C14-C18)-1,3-diaminopropane, based on a total weight of the liquid composition;
   from 35 weight % to 75 weight % of organic solvent, based on the total weight of the liquid composition; and
   from 0.20 weight % to 25 weight % of acid, based on the total weight of the liquid composition;
   wherein the organic solvent comprises propylene glycol; and
   wherein the acid is one or more acids selected from the group consisting of malic acid, benzoic acid, mandelic acid, lactic acid, acetic acid, succinic acid, tartaric acid, and citric acid.

2. The liquid composition of claim 1, wherein the composition comprises 2,2'-(octadecylimino)bisethanol.

3. The liquid composition of claim 1, wherein the composition comprises N,N,N'-tris(2-hydroxyethyl)-N'-alkyl/alkenyl(C14-C18)-1,3-diaminopropane.

4. The liquid composition of claim 2, wherein the composition comprises 70% or more of 2,2'-(octadecylimino)bisethanol.

5. The liquid composition of claim 2, wherein the 2,2'-(octadecylimino)bisethanol is produced from plant-derived stearic acid.

6. The liquid composition of claim 2, wherein the 2,2'-(octadecylimino)bisethanol is produced by reacting stearamine with ethylene oxide at an ethylene oxide:stearamine ratio of 2.0 to 2.20:1.

7. The liquid composition of claim 1, wherein the organic solvent consists of propylene glycol.

8. The liquid composition of claim 1, wherein the liquid composition comprises from 30 weight % to 55 weight % of the 2'-(octadecylimino)bis ethanol or N,N,N'-tris(2-hydroxyethyl)-N'-alkyl/alkenyl(C14-C18)-1,3-diaminopropane, optionally, wherein the liquid composition comprises from 35 weight % to 45 weight % of the organic solvent, and, further optionally, wherein the liquid composition comprises from 5 weight % to 15 weight % of the acid.

9. The liquid composition of claim 1, wherein the acid is one or more of malic acid, mandelic acid, lactic acid, acetic acid, succinic acid, tartaric acid, and citric acid.

10. The liquid composition of claim 1, wherein the acid is one or more of malic acid, lactic acid, and tartaric acid.

11. The liquid composition of claim 1, wherein the acid is malic acid or tartaric acid.

12. The liquid composition of claim 1, wherein the acid is a combination of malic acid and benzoic acid and/or mandelic acid.

13. The liquid composition of claim 1, wherein the liquid composition is ethanol-free.

14. The liquid composition of claim 1, consisting essentially of:
   2,2'-(octadecylimino)bisethanol;
   propylene glycol; and
   an acid selected from malic acid, tartaric acid, or mixtures thereof.

15. The liquid composition of claim 1, wherein the liquid composition is stable and free of precipitates after two weeks of storage at room temperature.

16. The liquid composition of claim 1, wherein the liquid composition is stable and free of precipitates after three months of storage at room temperature.

* * * * *